United States Patent
Ayer et al.

(10) Patent No.: US 7,427,266 B2
(45) Date of Patent: Sep. 23, 2008

(54) METHOD AND APPARATUS FOR VERIFICATION OF INGESTION

(75) Inventors: Steven M. Ayer, Marblehead, MA (US); Donald R. Denning, Jr., Shirley, MA (US); Frank C. Bomba, Andover, MA (US); Andrew D. Christian, Lincoln, MA (US); James E. Hicks, Jr., Newton, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 738 days.

(21) Appl. No.: 10/737,229

(22) Filed: Dec. 15, 2003

(65) Prior Publication Data

US 2005/0131281 A1 Jun. 16, 2005

(51) Int. Cl.
*A61B 5/07* (2006.01)
*A61B 5/103* (2006.01)
*A61B 5/117* (2006.01)

(52) U.S. Cl. ...................................... 600/302; 600/593
(58) Field of Classification Search ......... 600/300–302, 600/593
See application file for complete search history.

(56) References Cited

U.S. PATENT DOCUMENTS

| | | | | |
|---|---|---|---|---|
| 3,719,183 A | * | 3/1973 | Schwartz | 600/302 |
| 5,279,607 A | * | 1/1994 | Schentag et al. | 604/890.1 |
| 5,697,384 A | * | 12/1997 | Miyawaki et al. | 128/899 |
| 6,440,069 B1 | * | 8/2002 | Raymond et al. | 600/300 |
| 6,632,175 B1 | * | 10/2003 | Marshall | 600/309 |
| 6,711,423 B2 | * | 3/2004 | Colvin, Jr. | 600/317 |
| 6,800,060 B2 | * | 10/2004 | Marshall | 600/309 |
| 7,083,578 B2 | * | 8/2006 | Lewkowicz et al. | 600/593 |
| 2002/0132226 A1 | * | 9/2002 | Nair et al. | 435/4 |
| 2003/0191430 A1 | * | 10/2003 | D'Andrea et al. | 604/66 |
| 2003/0216622 A1 | * | 11/2003 | Meron et al. | 600/300 |

* cited by examiner

*Primary Examiner*—Charles A. Marmor, II
*Assistant Examiner*—Navin Natnithithadha

(57) ABSTRACT

A method and apparatus keeps track of ingestible objects (such as pills or food items) ingested by humans or animals. The objects are supplied with radio frequency identification (RFID) tags encoding data describing the objects. The humans or animals ingesting the objects are equipped with RFID sensors for detecting, decoding, and archiving the data encoded in the tags. A user may scan the body of the human or animal subject with a sensor to determine if a tagged object has been ingested. The tags may be covered with substances or contain elements that dissolve upon entering a digestive system. This allows detection of ingestion and also allows the RFID tag encoding to change in the course of digestion.

18 Claims, 5 Drawing Sheets

METHOD AND APPARATUS FOR VERIFICATION OF INGESTION

BACKGROUND OF THE INVENTION

Keeping track of objects swallowed by a human or an animal is necessary in many situations. For example, medical personnel may want to know what pills were taken by the patient and when. An individual or an attending medical professional may need a reminder in case a medication in not taken on time. Automated tracking of food and medicine intake by humans and animals has many applications, such as simplifying data logging during experiments with multiple live subjects or while providing medical or veterinary care.

SUMMARY OF THE INVENTION

Embodiments of this invention include an apparatus and a method for detecting ingestion of an object, comprising an ingestible object and an identification circuit coupled to the ingestible object. The identification circuit upon ingestion of the ingestible object is electromagnetically coupled to a sensing device to indicate ingestion of the ingestible object. The ingestion may be performed in medicinal purposes. The ingestion may be performed by a human.

The electromagnetic coupling may be a radio frequency electromagnetic coupling.

The electromagnetic coupling of the identification circuit may be different for at least two locations of the ingestible object. The locations may include a container and an ingestion system. An electromagnetic parameter of the identification circuit during the ingestion may be altered to alter the electromagnetic coupling. The identification circuit may comprise two layers, at least one of the layers being altered during the ingestion. This layer may be opaque to electromagnetic signals within a wavelength band and dissolved during the ingestion. Alternatively a part of the identification circuit may be dissolved during the ingestion.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
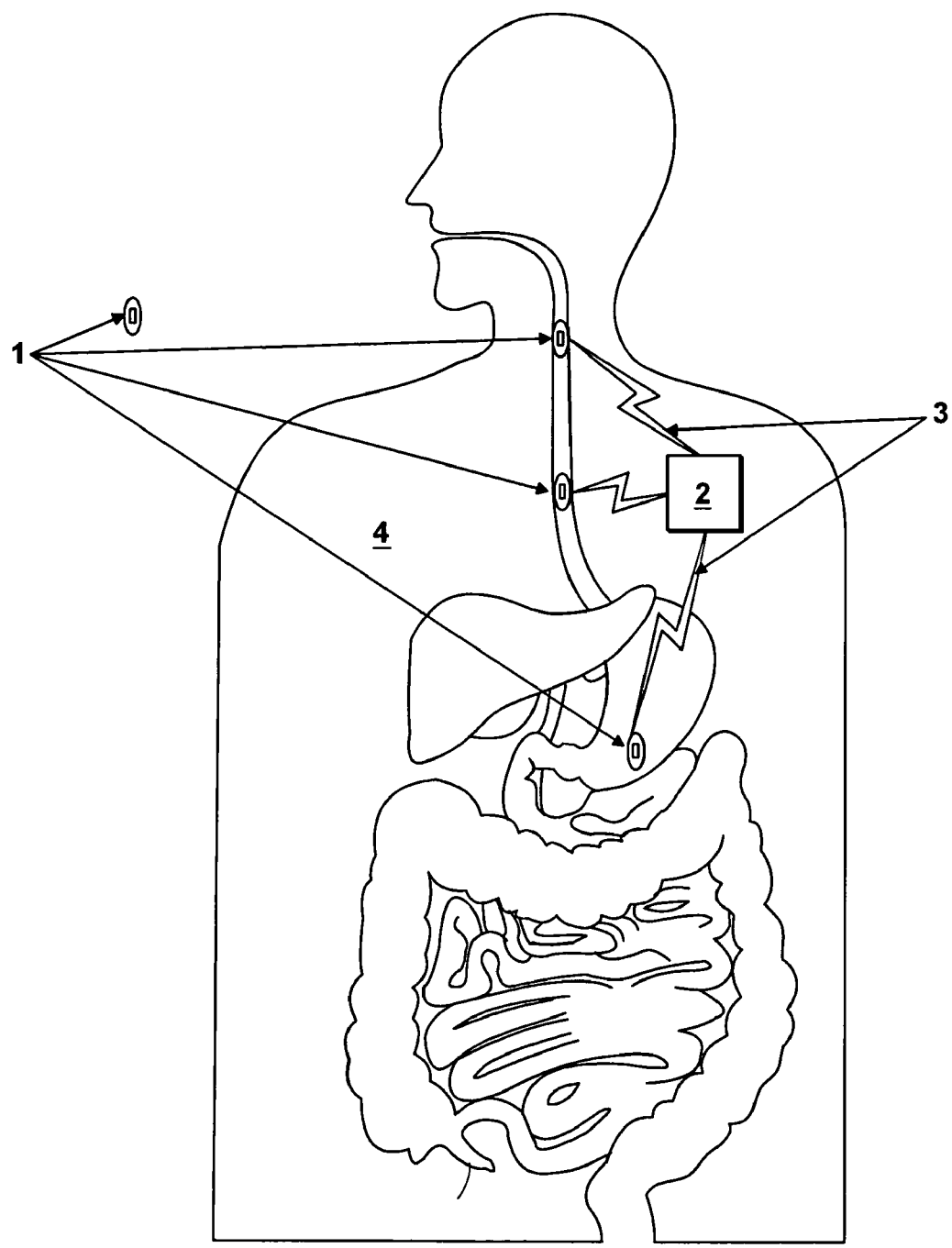
FIG. 1 is a schematic diagram showing the functioning of one embodiment of this invention.

FIG. 1 shows the functioning of one embodiment of this invention. A human 4 wearing a sensor 2 ingests an ingestible object 1. The electromagnetic coupling of sensor 2 to the ingestible object 1 is shown as signals or waves or the like 3. This coupling 3 occurs when the ingestible object 1 is inside the digestive tract of the human or animal subject 4. The sensor 2 upon such coupling may register the presence of the ingestible object 1 in the digestive tract. This registering may result in incrementing a counter showing the number of ingestible objects 1 ingested by the human or animal subject 4.

The ingestible object 1 may be a pill or a capsule containing a medical substance, a food item, a small monitoring device or any other object, the swallowing of which may need to be monitored.

Figure 2:
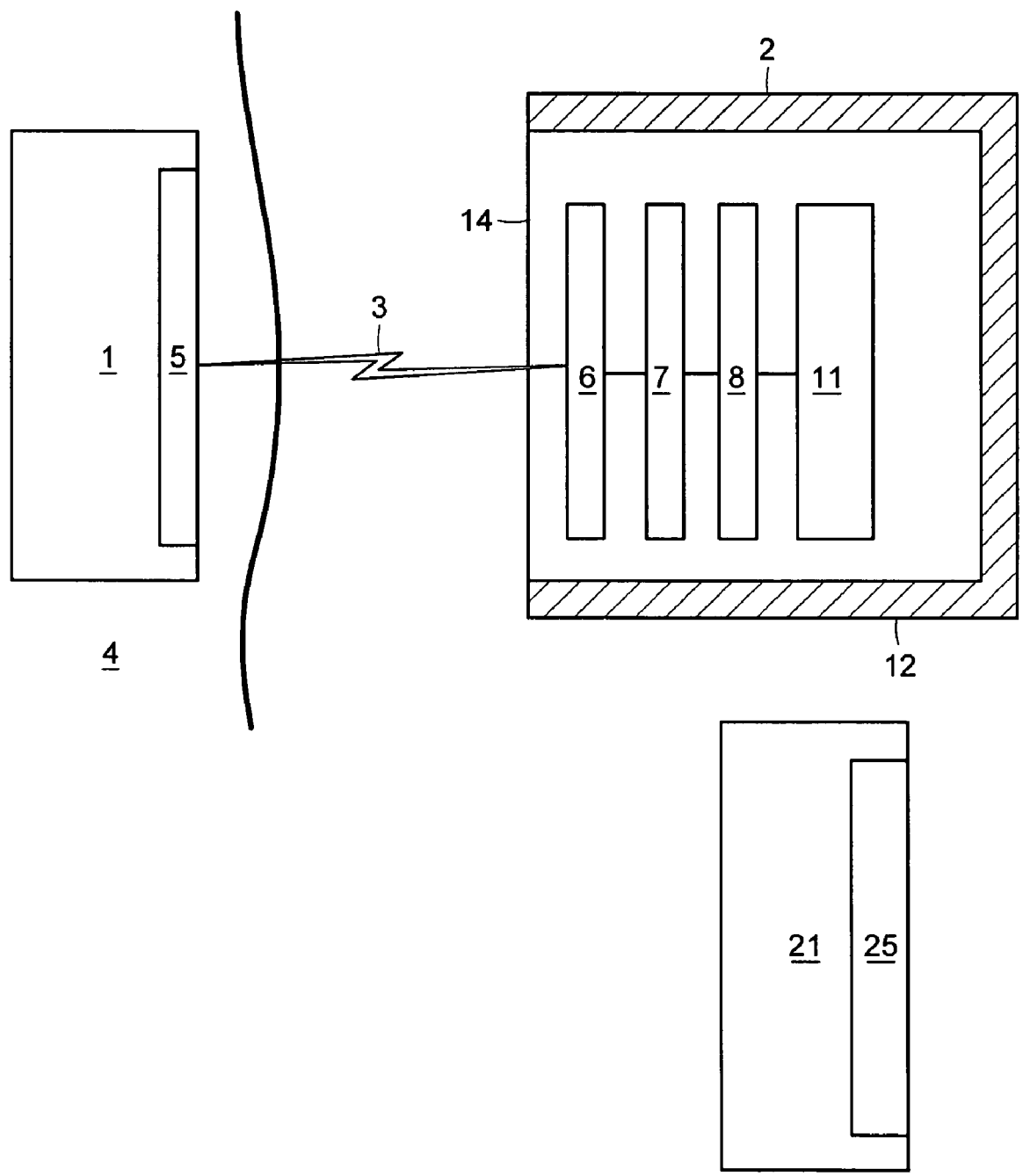
FIG. 2 is a schematic diagram showing the functioning of another embodiment of this invention.

One possible electromagnetic coupling mechanism may be the technology known as Radio Frequency Identification (RFID). In one embodiment of this invention using the RFID technology, a radio frequency circuit 5 (or RFID tag) is attached or embedded into the ingestible object 1, as shown in FIG. 2. The circuit 5 is electronically programmed with identifying information. In other words, the circuit 5 becomes a data carrier by being able to be configured in a number of ways, each distinct configuration representing, for example, a different identification number.

The data encoded in the circuit 5 may represent, for example, the manufacturer, the serial number, and/or the type of the object.

The circuit 5 may be implemented with the materials that do not harm the human or animal subjects 4. These materials allow the size of circuit 5 to be small enough to fit on ingestible objects 1 that can be swallowed and still permit encoding of sufficient amount of information to enable this invention. After the ingestion, the circuit 5 may dissolve in the digestive tract or pass through it and exit the human or animal subjects 4. The manufacturer of the ingestible object 1 may attach or embed into it the circuit 5. The circuit 5 may also be attached, embedded, or altered after the object 1 is manufactured to permit other parties more freedom in choosing the data for encoding and the encoding methods.

Continuing with FIG. 2, in order to establish electromagnetic coupling with the circuit 5, the sensor 2 may include an antenna or coil 6 and a transceiver 7 responsible for generating electromagnetic waves or radio waves transmitted by the antenna or coil 6. The electromagnetic coupling is mainly capacitive when an antenna is used and is mainly inductive when a coil is used.

The antenna or coil 6 emits radio waves with a limited effective distance range depending upon its power output and the radio frequency used. When the circuit 5 passes through the effective range of the electromagnetic field emitted by the antenna or coil 6, the circuit 5 according to its configuration alters the configuration of this field. This alteration depends on the data encoded in the circuit 5. The altered electromagnetic field is sensed or received by transmitter 7. In turn, the decoder 8 decodes the data encoded in the circuit by analyzing the sensed altered electromagnetic field. A computation device 11 in sensor 2 uses the decoded data to detect the presence and identity of the ingestible object 1 carrying the circuit 5. The computation device 11 may be for example a microprocessor or other digital processor or a data storage or data transmission device. The circuit 5 operates without an internal power source and uses the operating power generated by the sensor 2. Further details of the RFID technology are well known to those skilled in the pertinent art and are beyond the scope of this invention.

The sensor 2 may store the decoded data for a subsequent retrieval and archiving, it may keep count of the ingested objects, and it may inform the human 4 or other individuals or devices about the actions to be taken upon the ingestion. The timing of ingestion may also be recorded for each object 1. The sensor 2 may use a wired or wireless link or links for the communications necessary for its functioning. The sensor 2 may be attached to an appropriate location on the body of the human or animal subject 4, worn by the subject, or simply located in sufficient proximity.

Medical or veterinary personnel, attendants, or other users may use the sensor 2 to scan the body of the human or animal subject 4 to determine whether the human or animal subject 4 has ingested none, one, or several objects 1.

In other embodiments of this invention, the electromagnetic coupling 3 between the ingestible object 1 and the sensor 2 may be accomplished using electromagnetic waves of non-radio frequencies and/or using non-wave configurations of the electromagnetic field.

In the embodiment shown in FIG. 1., the electromagnetic coupling 3 between the ingestible object 1 and the sensor 2 does not occur until the ingestible object 1 is ingested. After the ingestion by the human or animal subject 4, the ingestible object 1 is positioned close enough to the sensor 2 for electromagnetic coupling and information acquisition by the sensor 2 to occur.

In the embodiment shown in FIG. 2, the sensor 2 is partially enclosed in an enclosure 12 opaque to electromagnetic waves coming from the directions other than an opening 14. The enclosure 12 substantially prevents electromagnetic coupling between the sensor 2 and the ingestible object until the object 1 is facing the opening 14 of the enclosure 12 and is close enough to the antenna or coil 6. This arrangement substantially prevents electromagnetic coupling 3 between the sensor 2 and the ingestible object 1 until the human or animal subject 4 ingests the ingestible object 1. In this embodiment no coupling and no information acquisition by the sensor 2 takes place until the human or animal subject 4 ingests the object 1. One advantage of this arrangement is that no information is acquired by the sensor 2 when an ingestible object 21 coupled with a circuit 25 is accidentally brought near it on the side covered with by the enclosure 12.

In embodiments similar to the embodiment shown in FIG. 2, instead of or in addition to the enclosure 12, the sensor 2 is equipped with a directional antenna 6 pointing in the direction 14. These embodiments substantially prevent electromagnetic coupling 3 between the sensor 2 and the ingestible object 1 until the human or animal subject 4 ingests the ingestible object 1. The functioning of these embodiments is similar to the functioning of the embodiment shown in FIG. 2.

Figure 3:
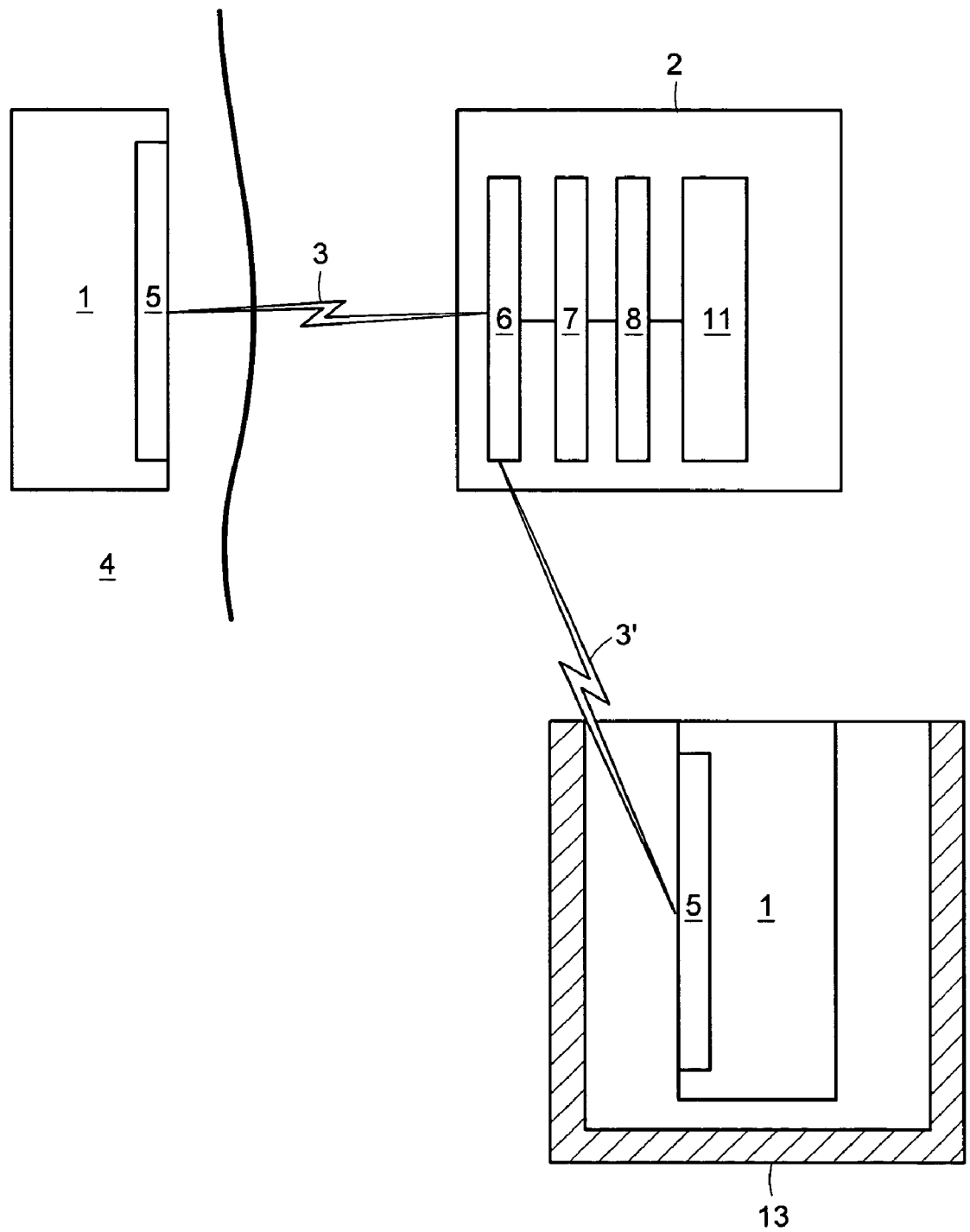
FIG. 3 is a schematic diagram showing the functioning of a third embodiment of this invention.

In the embodiment of this invention shown in FIG. 3, the ingestible object 1 before ingestion may be stored in a container 13. The container 13 alters the electromagnetic coupling between the sensor 2 and the ingestible object 1 so that the difference between the electromagnetic coupling 3 inside the human or animal subject 4 and the electromagnetic coupling 3' inside the container 13 may be detected by the sensor 2. This difference may be used as an indicator that the human or animal subject 4 has removed the ingestible object 1 from the container 13 and has ingested the ingestible object 1.

Figure 4:
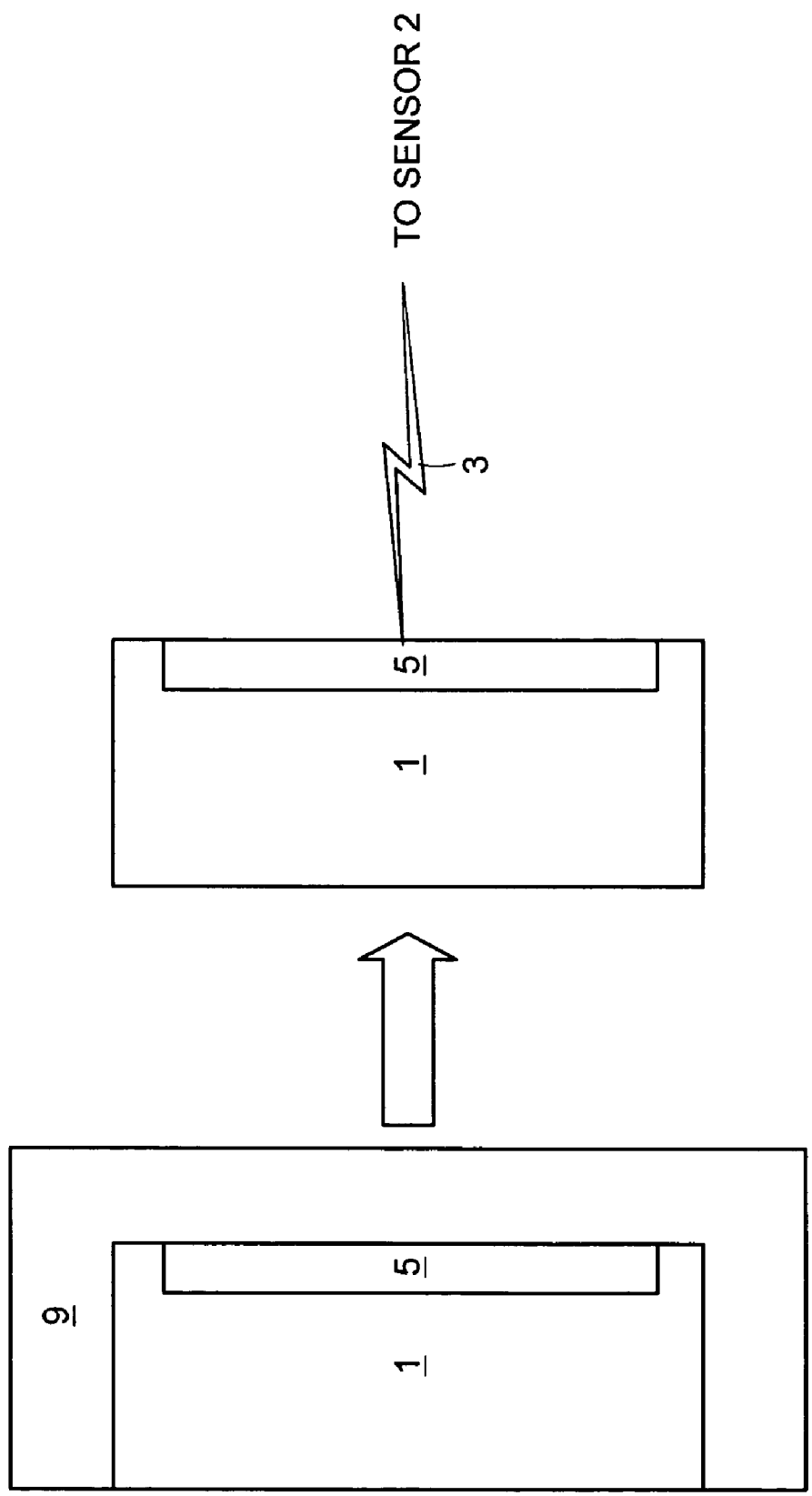
FIG. 4 is a schematic diagram showing the functioning of a fourth embodiment of this invention.
Figure 5:
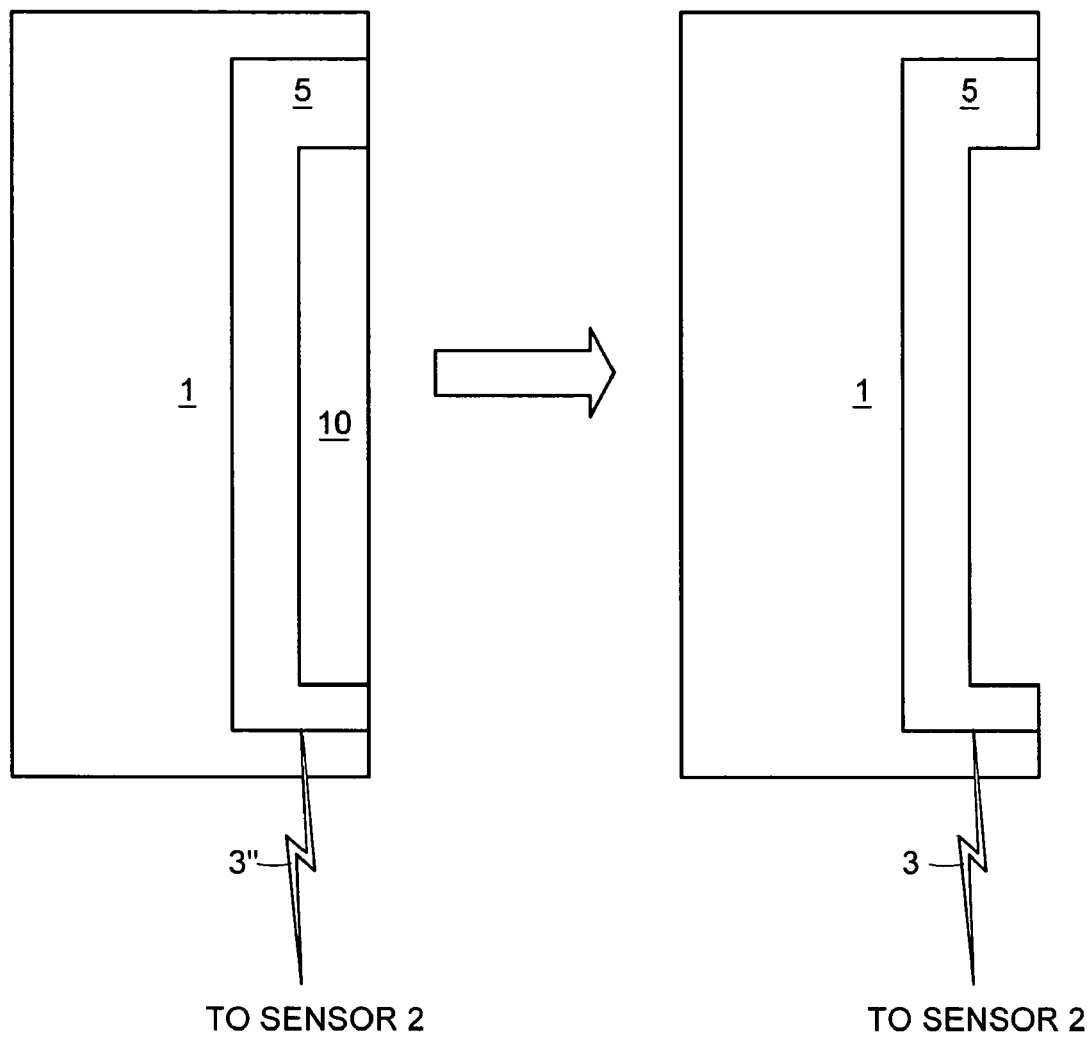
FIG. 5 is a schematic diagram showing the functioning of a fifth embodiment of this invention.

In other embodiments, an electromagnetic parameter of the circuit 5 is altered during ingestion, which in turn alters the electromagnetic coupling 3. As a result, the circuit 5 may use a variety of data carrying schemes. FIGS. 4 and 5 are illustrative. Given these examples, other combinations and variations are within the purview of one skilled in the art.

In the embodiment of this invention shown in FIG. 4, the ingestible object 1 is covered with a coating or layer 9, which is opaque to radio frequency waves and therefore prevents electromagnetic coupling 3 of the digestible object 1 with the sensor 2. After ingestion of the ingestible object 1 by the human or animal subject 4, the layer 9 is removed within the digestive system chemically, mechanically, or otherwise. For example, the layer 9 may be dissolved by saliva, stomach acid, or other substances coming in contact with the ingestible object 1 within the digestive tract of the human or animal subject 4. After the layer 9 is substantially removed, as illustrated in the right-hand side of FIG. 4, the electromagnetic coupling 3 between the ingestible object 1 and the sensor 2 becomes possible. In this embodiment, the sensor 2 obtains data encoded in the ingestible object 1 only after it is ingested and digested to the degree where layer 9 is effectively removed (dissolved) as illustrated in FIG. 4.

In the embodiment of this invention shown in FIG. 5, the circuit 5 embedded in the ingestible object 1 contains at least one circuit element 10, such that after ingestion of the ingestible object 1 by the human or animal subject 4, the element 10 is removed within the digestive system chemically, mechanically, or otherwise. For example, the element 10 may be dissolved or chemically altered from contact with saliva, stomach acid, or other substances coming in contact with the ingestible object 1 within the digestive tract of the human or animal subject 4. The electromagnetic coupling 3" and 3 between the sensor 2 and the circuit 5 differs before and after the removal of the circuit element 10. In other words, the removal of the element 10 from the circuit 5 changes the data encoded in the circuit 5. In this embodiment, the sensor 2 obtains data encoded in circuit 5 with the element 10 in the ingestible object 1 before it is ingested (electromagnetic coupling 3"), and the sensor 2 obtains different data encoded in the circuit 5 without the element 10 (having been effectively dissolved) after the object 1 is ingested (electromagnetic coupling 3). At each stage shown in FIG. 5, sensor 2 stores these two different obtained data or performs other actions based on these two data.

In other embodiments, the number of dissolvable layers and/or the number of dissolvable circuit elements may be greater than one and their removal may be spaced in time (e.g. they may dissolve at different rates). In such embodiments, as the object 1 is affected by the environment of the digestive system, several data are transmitted to the sensor 2 as different layers or elements are removed at different times. The data-carrying capacity of the circuit 5 is thus effectively increased.

The substances used to implement the dissolvable portions are chosen to minimize or eliminate any undesired side effects to the human or animal subject 4 ingesting the object 1. Example substances for layers 9 or circuit elements 10 include polymers, organic compounds, certain metals, etc.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of detecting ingestion of an ingestible object, comprising:

coupling an identification circuit to the ingestible object, the identification circuit upon ingestion of the ingestible object enabling electromagnetic coupling to a sensing device such that an electromagnetic field produced by the sensing device is altered by the identification circuit to indicate ingestion of the ingestible object; and monitoring electromagnetic coupling of the identification circuit to the sensing device to determine whether the ingestible object has been ingested, wherein the ingestible object includes a layer that is opaque to electromagnetic signals within a wavelength band and configured to be dissolved as a result of the ingestion, to produce a change in the electromagnetic coupling to the sensing device, thereby indicating that the ingestible object has been ingested.

2. The method of claim 1 wherein the ingestion is performed for medicinal purposes.

3. The method of claim 1 wherein the ingestion is human ingestion.

4. The method of claim 1 wherein the electromagnetic coupling is radio frequency electromagnetic coupling.

5. The method of claim 1 wherein an electromagnetic parameter of the identification circuit during the ingestion is altered to alter the electromagnetic coupling.

6. The method of claim 5 wherein at least one part of the identification circuit is dissolved during the ingestion.

7. The method of claim 1 wherein coupling is repeated a plurality of times to couple a plurality of identification circuits to a plurality of ingestible objects such that each identification circuit is coupled to a respective ingestible object, and wherein the method further comprises incrementing a counter after ingestion of each ingestible object.

8. An apparatus for use with a sensing device to detect ingestion, comprising:
   an ingestible object; and
   an identification circuit coupled to the ingestible object, the identification circuit enabling electromagnetic coupling to the sensing device such that an electromagnetic field produced by the sensing device can be altered by the identification circuit,
   wherein the ingestible object includes a layer that is opaque to electromagnetic signals within a wavelength band and configured to be dissolved during ingestion, to produce a change in electromagnetic coupling to the sensing device, thereby indicating that the ingestible object has been ingested.

9. The apparatus of claim 8 wherein the ingestion is performed for medicinal purposes.

10. The apparatus of claim 8 wherein the ingestion is human ingestion.

11. The apparatus of claim 8 wherein the electromagnetic coupling is radio frequency electromagnetic coupling.

12. A method of detecting ingestion of ingestible objects, comprising:
   coupling a plurality of identification circuits to a plurality of ingestible objects such that each identification circuit is coupled to a respective ingestible object, each identification circuit upon ingestion of the respective ingestible object enabling electromagnetic coupling to a sensing device such that an electromagnetic field produced by the sensing device is altered by the identification circuit to indicate ingestion of the respective ingestible object;
   monitoring electromagnetic coupling of the identification circuits to the sensing device to determine whether an ingestible object has been ingested; and
   incrementing a counter after ingestion of each ingestible object.

13. The method of claim 12 wherein the ingestion is performed for medicinal purposes.

14. The method of claim 12 wherein the ingestion is human ingestion.

15. The method of claim 12 wherein the electromagnetic coupling is radio frequency electromagnetic coupling.

16. The method of claim 12 wherein the electromagnetic coupling of each identification circuit is different for at least two different locations of the respective ingestible object, and wherein one of the at least two different locations is inside a container for storage of the ingestible objects before ingestion and another of the at least two different locations is in an ingestion system.

17. The method of claim 12 wherein an electromagnetic parameter of each identification circuit is altered by ingestion of the identification circuit to alter the electromagnetic coupling.

18. The method of claim 12 wherein at least one part of each identification circuit is dissolved by ingestion.

* * * * *